US009033964B2

(12) United States Patent
Cho et al.

(10) Patent No.: US 9,033,964 B2
(45) Date of Patent: May 19, 2015

(54) TARGET STRUCTURE USED FOR GENERATING CHARGED PARTICLE BEAM, METHOD OF MANUFACTURING THE SAME AND MEDICAL APPLIANCE USING THE SAME

(75) Inventors: Seong-Mok Cho, Daejeon (KR); Moon Youn Jung, Daejeon (KR); Seunghwan Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 39 days.

(21) Appl. No.: 13/822,378

(22) PCT Filed: Sep. 30, 2011

(86) PCT No.: PCT/KR2011/007258
§ 371 (c)(1), (2), (4) Date: Mar. 12, 2013

(87) PCT Pub. No.: WO2012/046977
PCT Pub. Date: Apr. 12, 2012

(65) Prior Publication Data
US 2013/0172865 A1      Jul. 4, 2013

(30) Foreign Application Priority Data

Oct. 6, 2010  (KR) .................. 10-2010-0097299
Jan. 14, 2011  (KR) .................. 10-2011-0004195

(51) Int. Cl.
G21K 5/04      (2006.01)
A61B 18/20     (2006.01)
A61N 5/10      (2006.01)
H05H 6/00      (2006.01)

(52) U.S. Cl.
CPC ................ G21K 5/04 (2013.01); A61B 18/201 (2013.01); A61N 5/1077 (2013.01); A61N 2005/1088 (2013.01); H05H 6/00 (2013.01)

(58) Field of Classification Search
CPC ........... B32B 9/04; H01L 49/00; H01J 23/00; H01J 3/14; C23C 16/00
USPC .................. 428/446; 250/288, 423 P, 396 R; 118/728; 606/9–13, 16–18
See application file for complete search history.

(56) References Cited

U.S. PATENT DOCUMENTS 4,204,117 A    5/1980   Aberle et al.
6,137,110 A   10/2000   Pellin et al.
(Continued)

FOREIGN PATENT DOCUMENTS

WO    WO 2006086084 A2 *  8/2006

OTHER PUBLICATIONS

H. Schwoerer et al., "Laser-plasma acceleration of quasi-monoenergetic protons from microstructured targets", Nature, Jan. 26, 2006, pp. 445-448, vol. 439.

Primary Examiner — Ahmed Farah
Assistant Examiner — Victor Shapiro
(74) Attorney, Agent, or Firm — Rabin & Berdo, P.C.

(57) ABSTRACT

Provided are a target structure used for generating a charged particle beam, a method of manufacturing the same, and a medical appliance using the same. The target structure includes a target layer and a support having a through hole used as a progressing path of a laser beam or a charged particle beam.

11 Claims, 13 Drawing Sheets

(56) References Cited

U.S. PATENT DOCUMENTS

| | | | |
|---|---|---|---|
| 6,150,031 A * | 11/2000 | Yonehara | 428/446 |
| 6,444,980 B1 | 9/2002 | Kawato et al. | |
| 6,509,070 B1 | 1/2003 | Voevodin et al. | |
| 6,852,985 B2 * | 2/2005 | Cowan et al. | 250/423 P |
| 6,867,419 B2 | 3/2005 | Tajima | |
| 7,642,521 B2 * | 1/2010 | Willi et al. | 250/396 R |
| 7,816,646 B1 * | 10/2010 | Willoughby et al. | 250/288 |
| 2003/0183774 A1 | 10/2003 | Tajima | |
| 2005/0103275 A1 * | 5/2005 | Sasaki et al. | 118/728 |
| 2009/0230318 A1 | 9/2009 | Fourkal et al. | |

\* cited by examiner

TARGET STRUCTURE USED FOR GENERATING CHARGED PARTICLE BEAM, METHOD OF MANUFACTURING THE SAME AND MEDICAL APPLIANCE USING THE SAME

TECHNICAL FIELD

The present invention disclosed herein relates to a target structure used for generating a charged particle beam, a method of manufacturing the same and a medical appliance using the same.

BACKGROUND ART

A therapy using a charged particle beam receives attention as a treatment having good prognosis because the therapy can accurately attack cancer cells while minimizing damages of normal tissue. Typically, high-cost as well as large-sized accelerator and gantry have been required in order to generate a charged particle beam. However, a method of generating a charged particle beam by using a high-power pulsed laser has been recently suggested such that great reduction in size and cost of a therapeutic apparatus is anticipated.

In order to actually commercialize the therapy, energy of the charged particle beam has to be sufficiently large and energy distribution thereof has to be sufficiently small. Such requirements related to the energy and the energy distribution of the charged particles are easily satisfied as a thickness of a target layer irradiated by a laser becomes thinner. In particular, generation of the charged particles using a radiation pressure acceleration (RPA) mechanism requires a thin target layer having a thickness of 1 μm or less. However, when the thickness of the target layer is thin, accurate control of the position of the target layer is difficult as well as difficulties in handling of the target layer are increased.

DISCLOSURE OF THE INVENTION

Technical Problem

The present invention provides a target structure capable of improving structural stability of a thin target layer.

The present invention also provides a method of stably manufacturing a target structure having a thin target layer.

The present invention also provides a medical appliance using a charged particle beam generated from a thin target layer.

Technical Solution

Embodiments of the present invention provide a target structure in which a target layer is formed on a support. The target structure may include a target layer having a first surface irradiated by a laser beam and a second surface emitting a charged particle beam, and a support having a through hole used as a progressing path of the laser beam or the charged particle beam.

In some embodiments, the support is attached to the first surface of the target layer and the through hole may be used as the progressing path of the laser beam. In other embodiments, the support is attached to the second surface of the target layer and the through hole may be used as the progressing path of the charged particle beam.

In still other embodiments, the target layer is formed to a thickness range of about 0.001 μm to about 10 μm, and the support includes at least one of silicon, sapphire, diamond, quartz, glass, ceramic materials, or metallic materials and may be formed to a thickness of at least about 100 μm.

In even other embodiments, the support may include a material having a single crystal structure, and a surface of the support contacting the target layer may be a (100) plane. In this case, the through hole may include a region having a width that gradually increases away from the target layer.

In yet other embodiments, the target layer may include at least one inert metal.

In further embodiments, the target structure may further include an intermediate layer disposed between the target layer and the support. In this case, the intermediate layer has an intermediate through hole exposing the target layer and the intermediate through hole may be aligned to the through hole of the support. Also, the target layer may include at least one of inert metals, aluminum, titanium, polymethyl methacrylate (PMMA), polydimethylsiloxane (PDMS), polyimide, photoresist, or hydrogenated amorphous silicon.

In still further embodiments, the target layer may include a first target layer and a second target layer formed of materials different from each other. The first target layer constitutes the first surface irradiated by the laser beam and the second target layer may constitute the second surface emitting the charged particle beam. At this time, the second target layer constitutes a plurality of emitting patterns formed on a surface of the second target layer and spaced apart from each other, wherein the each emitting pattern has a width smaller than that of the through hole. In addition, the first target layer is formed of at least one metallic material, and the second target layer may be formed of at least one of polymethyl methacrylate (PMMA), polydimethylsiloxane (PDMS), polyimide, photoresist, or hydrogenated amorphous silicon.

In even further embodiments of the present invention, a medical appliance using a target layer formed on a support to generate a charged particle beam is provided. The medical appliance may include: a target structure, a light source irradiating a laser beam to the target structure, and a guiding structure guiding a charged particle beam emitted from the target structure to a biological object. At this time, the target structure includes a target layer formed on a support, and the support has a through hole used as a progressing path of the laser beam or the charged particle beam.

In yet further embodiments, the target layer is formed to a thickness range of about 0.001 μm to about 10 μm, and the support includes at least one of silicon, sapphire, diamond, quartz, glass, ceramic materials, or metallic materials and may be formed to a thickness of at least about 100 μm.

In much further embodiments, the target layer may include at least one of inert metals, aluminum, titanium, polymethyl methacrylate (PMMA), polydimethylsiloxane (PDMS), polyimide, photoresist, or hydrogenated amorphous silicon.

In still much further embodiments, the medical appliance may further include an intermediate layer disposed between the target layer and the support. The intermediate layer has an intermediate through hole exposing the target layer and the intermediate through hole may be aligned to the through hole of the support.

In even much further embodiments, the target layer may include a first target layer to which the laser beam is irradiated and a plurality of emitting patterns formed on a surface of the first target layer and spaced apart from each other. The each emitting pattern has a width smaller than that of the through hole of the support.

In yet much further embodiments, the first target layer is formed of at least one metallic material, and the emitting patterns may be formed of at least one of polymethyl methacrylate (PMMA), polydimethylsiloxane (PDMS), polyimide, photoresist, or hydrogenated amorphous silicon.

In some embodiments, the light source may be configured to irradiate a laser beam having an intensity of about $10^{18}$ W/cm$^2$ to the target layer.

In other embodiments, the guiding structure may include an accelerator accelerating the charged particle beam.

In still other embodiments of the present invention, a method of manufacturing a target structure including forming of a target layer on a support is provided. The method includes forming a target layer having a thickness range of about 0.001 µm to about 10 µm on a top surface of a support, forming a mask pattern exposing a portion of a bottom surface of the support on the bottom surface of the support, and then forming a through hole exposing the target layer by patterning the support using the mask pattern as an etch mask.

In even other embodiments, the support is a silicon wafer having a (100) plane bottom surface and the forming of the through hole may include wet etching an exposed bottom surface of the support by using an etch recipe having an etch selectivity with respect to the target layer. In addition, the wet etching may be performed by using at least one of tetramethyl ammonium hydroxide (TMAH), ethylene diamine pyrocatechol (EDP), or KOH as an etching solution. According to the foregoing embodiments, the target layer may include at least one inert metal.

In yet other embodiments, the etch stop layer may be further formed before the forming of the target layer. In this case, the forming of the through hole may include etching the etch stop layer using an etch recipe having an etch selectivity with respect to the target layer, after etching the support using an etch recipe having an etch selectivity with respect to the etch stop layer. According to the foregoing embodiments, the target layer may include at least one of inert metals, aluminum, titanium, polymethyl methacrylate (PMMA), polydimethylsiloxane (PDMS), polyimide, photoresist, or hydrogenated amorphous silicon.

Meanwhile, the forming of the target layer may include forming a metal layer formed of at least one metallic material and forming emitting patterns formed of at least one of polymethyl methacrylate (PMMA), polydimethylsiloxane (PDMS), polyimide, photoresist, or hydrogenated amorphous silicon. In further embodiments, the emitting patterns are formed on the metal layer after the forming of the metal layer and the through hole may be formed to expose a bottom surface of the metal layer. In still further embodiments, the emitting patterns are formed on the support before the forming of the metal layer and the through hole may be formed to expose bottom surfaces of the emitting patterns.

Advantageous Effects

According to the embodiments of the present invention, a target layer is formed on a support thicker than the target layer, and the support is formed to have a through hole exposing the target layer. Since the target layer is structurally supported by the support, a target structure according to the present invention may have a structural stability even though the target layer is formed very thin.

According to some embodiments, an etch stop layer may be disposed between the target layer and the support. In this case, the technical restrictions of the target materials and/or a thin film structure may be alleviated because technical limitations in that the target layer suffers etching damages during the formation of a through hole may be prevented.

MODE FOR CARRYING OUT THE INVENTION

The above objects, other objects, features and advantages of the present invention will be better understood from the following description of preferred embodiments taken in conjunction with the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art.

In the specification, it will be understood that when a layer (or film) is referred to as being 'on' another layer or substrate, it can be directly on the other layer or substrate, or intervening layers may also be present. Also, in the figures, the dimensions of layers and regions are exaggerated for clarity of illustration. Also, though terms like a first, a second, and a third are used to describe various regions and layers in various embodiments of the present invention, the regions and the layers are not limited to these terms. These terms are used only to discriminate one region or layer from another region or layer. Therefore, a layer referred to as a first layer in one embodiment can be referred to as a second layer in another embodiment. An embodiment described and exemplified herein includes a complementary embodiment thereof.

Figure 1:
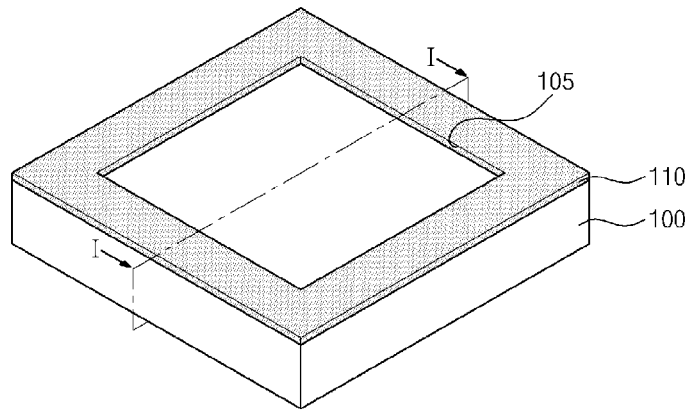
FIGS. 1, 3 and 5 are perspective views illustrating a method of manufacturing a target structure according to a first embodiment of the present invention.
Figure 2:
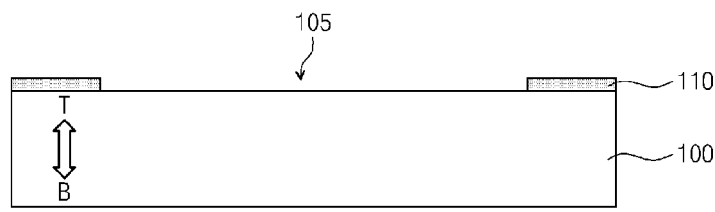
FIGS. 2, 4 and 6 are cross-sectional views illustrating the method of manufacturing a target structure according to the first embodiment of the present invention.
Figure 3:
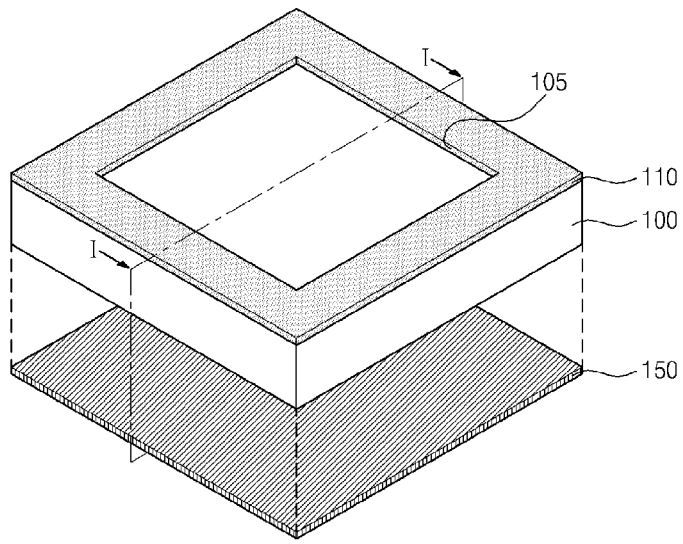
Figure 4:
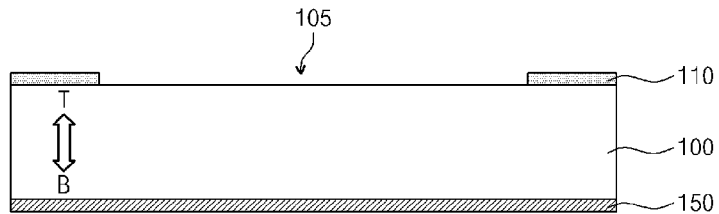
Figure 5:
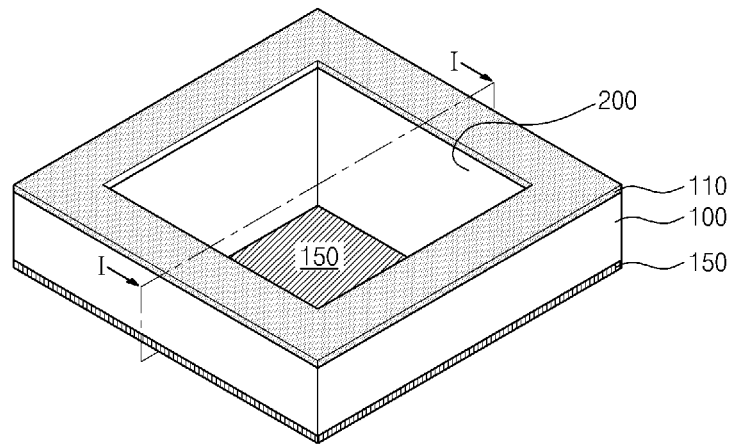
Figure 6:
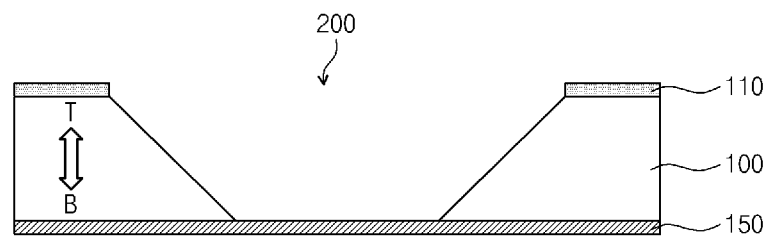

FIGS. 1, 3 and 5 are perspective views illustrating a method of manufacturing a target structure according to a first embodiment of the present invention, and FIGS. 2, 4 and 6 are cross-sectional views illustrating the method of manufacturing a target structure according to the first embodiment of the present invention. In particular, FIGS. 2, 4 and 6 illustrate cross-sections shown along the dotted lines 'I-I' of FIGS. 1, 3 and 5, respectively.

Referring to FIGS. 1 and 2, a mask pattern 110 is formed on a support 100. The mask pattern 110 may be formed to have an opening 105 exposing a top surface T of the support 100.

According to an embodiment of the present invention, the support 100 may be formed of a material having a single crystal structure. For example, the support 100 may be single crystal silicon. In this case, the top surface T of the support 100 may be a (100) plane in terms of a crystal structure.

However, the technical idea of the present invention is not limited by the material or the crystal structure of the support 100. For example, according to other embodiments of the present invention, the support 100 may be at least one of silicon, sapphire, diamond, quartz, glass, ceramic materials, or metallic materials, and the crystal structure thereof may be single crystalline, polycrystalline, or amorphous.

The support 100 may be formed to a thickness range of about a few hundred micrometers to about a few millimeters. According to some embodiments, the support 100 may be formed to a thickness of at least about 100 micrometers. The thickness of the support 100 may be adjusted through a polishing or grinding process.

The mask pattern 110 may be formed of a material having an etch selectivity with respect to the support 100. That is, the mask pattern 110 may include one material capable of having an etch resistance in an etching process etching the support 100. For example, when the support 100 is silicon, the mask pattern 110 may include at least one of silicon oxide, silicon nitride, or organic polymer materials.

Referring to FIGS. 3 and 4, a target layer 150 is formed on a bottom surface B of the support 100. Therefore, the support 100 is disposed between the target layer 150 and the mask pattern 110.

The target layer 150 may be at least one of metallic materials or compounds thereof. For example, the target layer 150 may include at least one inert metal such as platinum, gold, or silver. The target layer 150 may be formed to a thickness range of about 0.001 µm to about 10 µm. According to some embodiments, the target layer 150 may be formed to a thickness range of about 0.001 µm to about 1 µm. Since the target layer 150 is supported by the thicker support 100, the target layer 150 may not be damaged despite a small thickness thereof.

The target layer 150 may be formed by using one of various methods for forming a thin film. For example, the target layer 150 may be formed by using a chemical vapor deposition, physical vapor deposition, or electroplating method. However, the technical idea of the present invention is not limited by the method of forming the target layer 150.

Referring to FIGS. 5 and 6, a through hole 200 penetrating the support 100 to expose the target layer 150 is formed. The through hole 200 may be formed by etching the top surface T of the support 100 exposed by the opening 105.

More particularly, the forming of the through hole 200 may include etching the support 100 by using the mask pattern 110 as an etch mask. An etch recipe used in the etching may be selected to have an etch selectivity with respect to the mask pattern 110 and the target layer 150. According to some embodiments, when the support 100 is single crystal silicon, the etching may be performed by using at least one of tetramethyl ammonium hydroxide (TMAH), ethylene diamine pyrocatechol (EDP), or KOH as an etching solution. In this case, as shown in FIG. 6, sidewalls of the through hole 200 may be formed to have a slope with respect to an upper surface of the target layer 150.

However, as described above, since the technical idea of the present invention is not limited by the material or the crystal structure of the support 100, the etching is also not limited by the method exemplified above. For example, the through hole 200 may be formed through a dry etching method, a method performing a combination of dry etching and wet etching, or a method performing a combination of laser drilling and wet etching.

Figure 7:
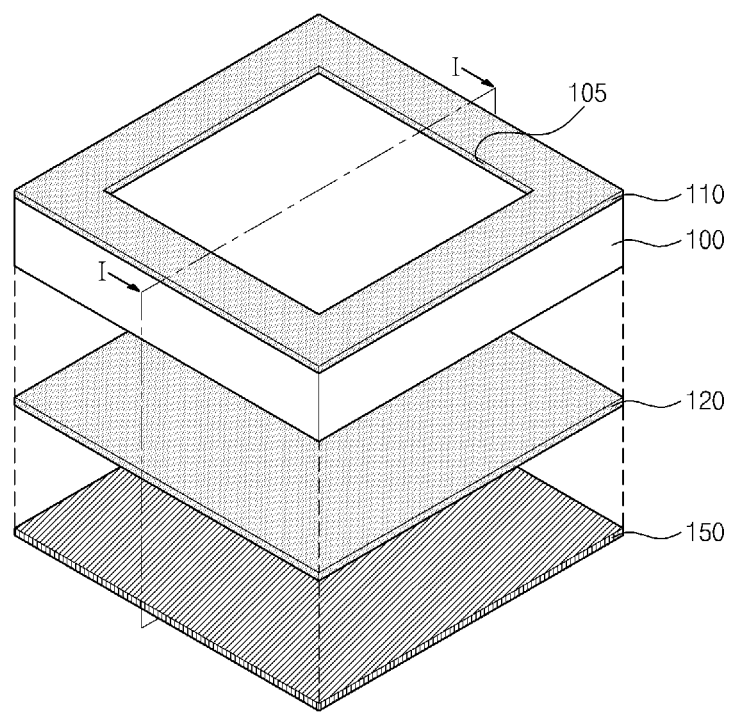
FIGS. 7, 9 and 11 are perspective views illustrating a method of manufacturing a target structure according to a second embodiment of the present invention.
Figure 8:
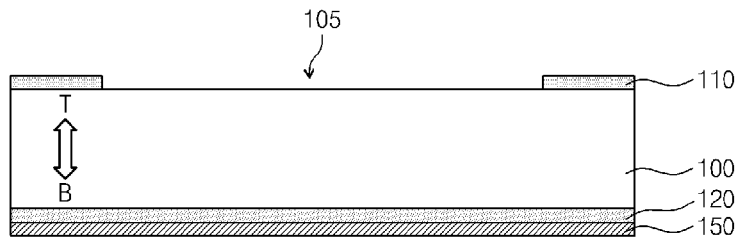
FIGS. 8, 10 and 12 are cross-sectional views illustrating the method of manufacturing a target structure according to the second embodiment of the present invention.
Figure 9:
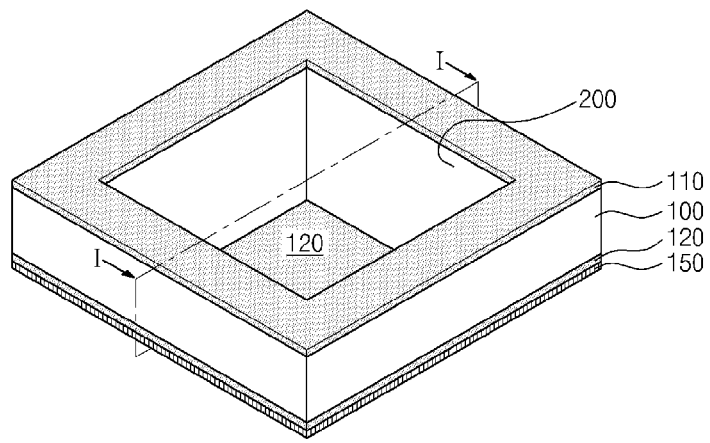
Figure 10:
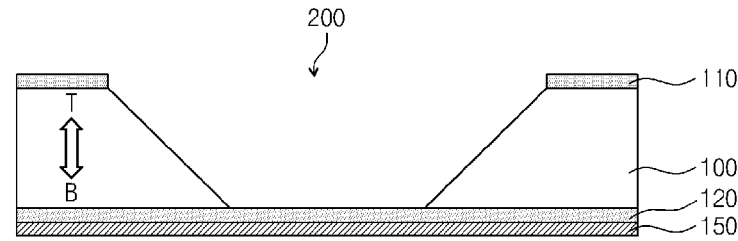
Figure 11:
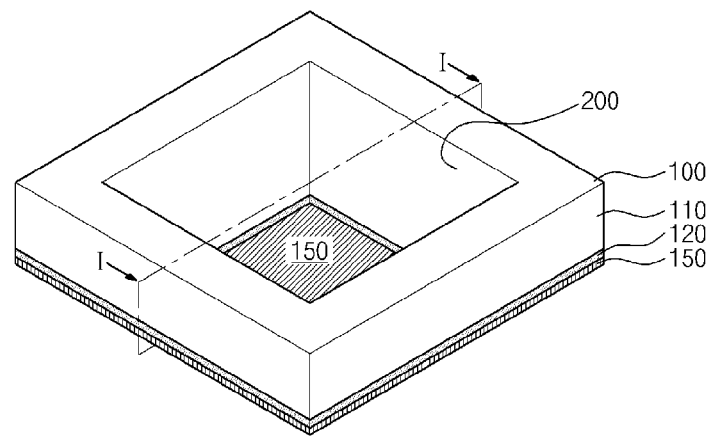
Figure 12:
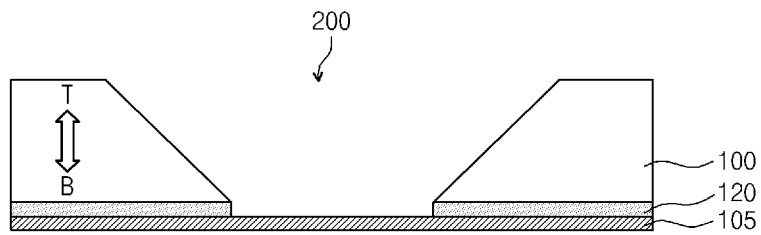

FIGS. 7, 9 and 11 are perspective views illustrating a method of manufacturing a target structure according to a second embodiment of the present invention, and FIGS. 8, 10 and 12 are cross-sectional views illustrating the method of manufacturing a target structure according to the second embodiment of the present invention. In particular, FIGS. 8, 10 and 12 illustrate cross-sections shown along the dotted lines 'I-I' of FIGS. 7, 9 and 11, respectively. For the simplicity of the description, the description related to the technical characteristics overlapping with the foregoing first embodiment may not be provided.

Likewise the foregoing embodiment, the mask pattern 110 is formed on the top surface T of the support 100, and the target layer 150 is formed on the bottom surface B of the support 100. However, according to the present embodiment, forming an etch stop layer 120 on the bottom surface B of the support 100 may be further performed before the forming of the target layer 150. Therefore, as shown in FIGS. 7 and 8, the etch stop layer 120 may be disposed between the support 100 and the target layer 150.

The etch stop layer 120 may be formed of a material having an etch selectivity with respect to the support 100. That is, the etch stop layer 120 may include at least one material capable of having an etch resistance in an etching process etching the support 100. For example, when the support 100 is silicon, the etch stop layer 120 may include at least one of silicon oxide, silicon nitride, or organic polymer materials. Therefore, as shown in FIGS. 9 and 10, etching of the target layer 150 may be prevented during the forming of the through hole 200 by etching the support 100.

Since the damage of the target layer 150 may be prevented during the forming of the through hole 200, the target layer 150 may be formed of more various materials than those of the foregoing first embodiment. That is, according to the etch stop layer 120, restrictions with respect to the type of a material usable for the target layer 150 may be greatly alleviated. For example, according to the present embodiment, the target layer 150 may be formed of platinum, gold, silver, aluminum, titanium, or hydrogenated amorphous silicon, or may further include at least one of polymethyl methacrylate (PMMA), polydimethylsiloxane (PDMS), polyimide, or photoresist.

Thereafter, as shown in FIGS. 11 and 12, the target layer 150 is exposed by selectively etching the etch stop layer 120 exposed by the through hole 200. That is, an intermediate through hole exposing the target layer 150 by being aligned with the through hole 200 is formed in the etch stop layer 120. Meanwhile, the etch stop layer 120 may be a material that may be selectively removed by minimizing etching damage with respect to the target layer 150, and in this case, the target layer 150 may be exposed by the through hole 200 without having etching damage.

Meanwhile, according to some embodiments, the etch stop layer 120 may not have an etch selectivity with respect to the mask pattern 110. In this case, the mask pattern 110 is etched during the exposing of the target layer 150 or the mask pattern 110 is removed such that the top surface T of the support 100 may be exposed as shown in FIGS. 11 and 12.

FIGS. 13, 15, 17 and 19 are perspective views illustrating a method of manufacturing a target structure according to a third embodiment of the present invention, and FIGS. 14, 16, 18 and 20 are cross-sectional views illustrating the method of manufacturing a target structure according to the third embodiment of the present invention. In particular, FIGS. 14, 16, 18 and 20 illustrate cross-sections shown along the dotted lines 'I-I' of FIGS. 13, 15, 17 and 19, respectively. For the simplicity of the description, the description related to the technical characteristics overlapping with the foregoing first and second embodiments may not be provided.

Figure 13:
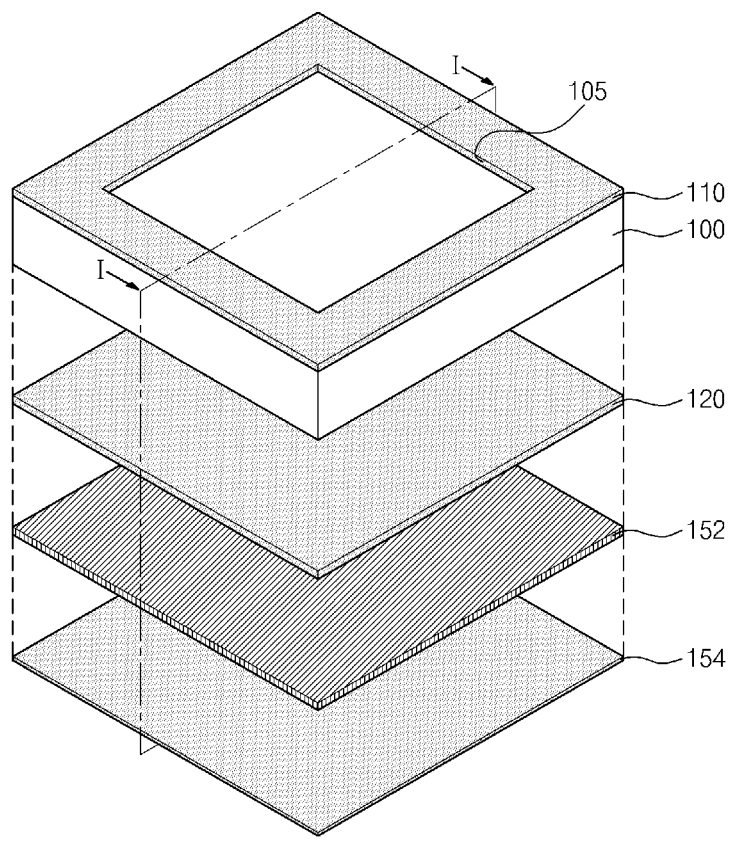
FIGS. 13, 15, 17 and 19 are perspective views illustrating a method of manufacturing a target structure according to a third embodiment of the present invention.
Figure 14:
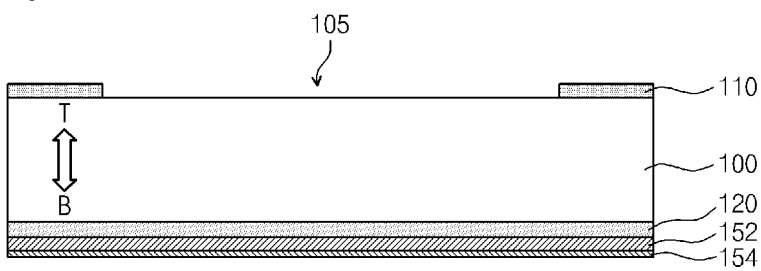
FIGS. 14, 16, 18 and 20 are cross-sectional views illustrating the method of manufacturing a target structure according to the third embodiment of the present invention.

Likewise the foregoing embodiment described with reference to FIGS. 7, 9 and 11, the mask pattern 110 is formed on the top surface T of the support 100, and the etch stop layer 120 and the target layer is sequentially formed on the bottom surface B of the support 100. However, according to the present embodiment, the target layer may include a first target layer 152 and a second target layer 154 that are formed of materials different from each other as shown in FIGS. 13 and 14.

Figure 15:
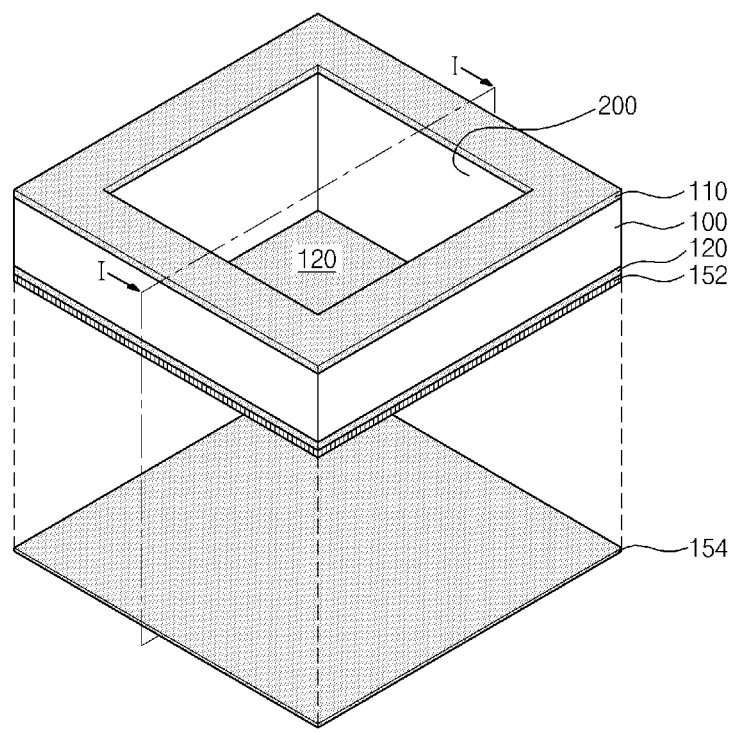
Figure 16:
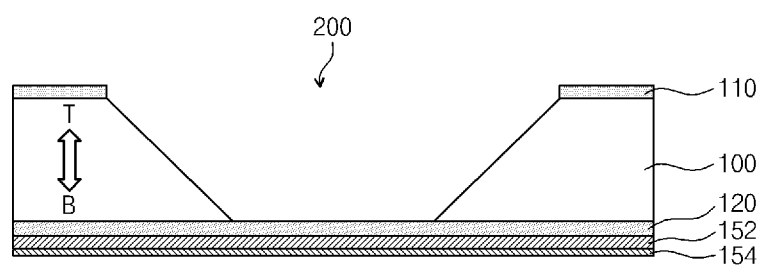

Referring to FIGS. 15 and 16, the through hole 200 penetrating the support 200 to expose the etch stop layer 120 is formed. Since the etch stop layer 120 is formed of a material having an etch selectivity with respect to the support 100, the through hole 200 may be formed without having etching damage with respect to the first target layer 152. In addition, likewise the foregoing second embodiment, the first target layer 152 may not have restrictions with respect to the type of a material usable by preventing the etching damage with respect to the first target layer 152. According to some embodiments, the first target layer 152 may be formed of platinum, gold, silver, aluminum, titanium, or hydrogenated amorphous silicon.

Figure 17:
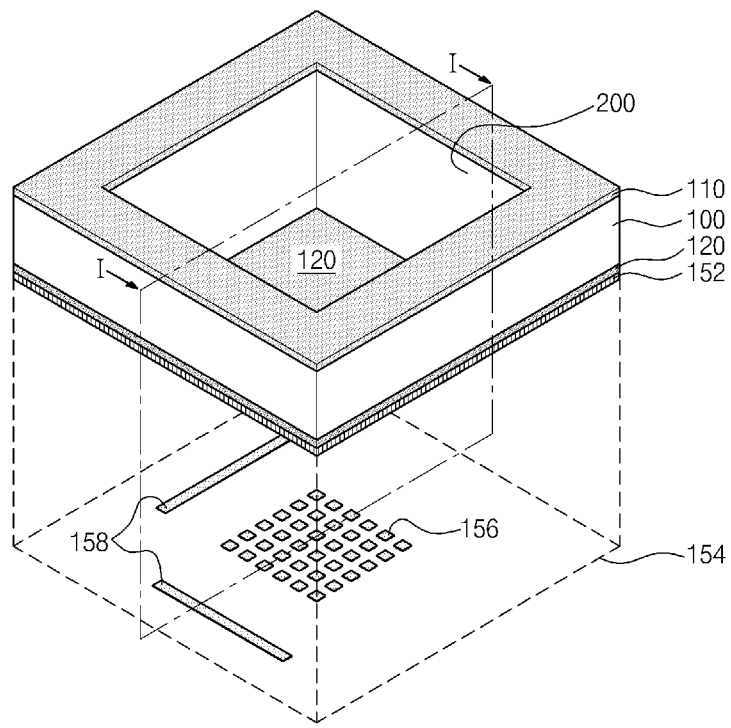
Figure 18:
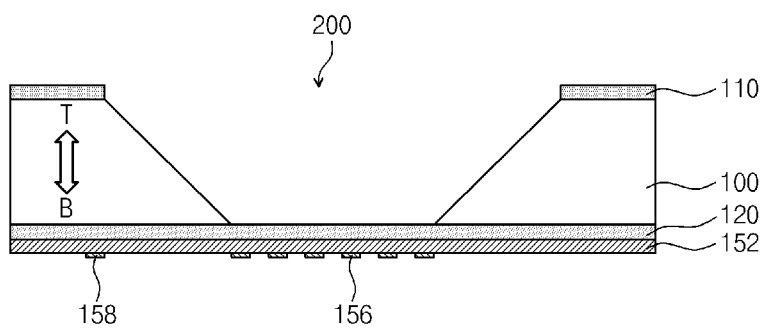

Referring to FIGS. 17 and 18, emitting patterns 156 and alignment patterns 158 are formed by patterning the second target layer 154. According to some embodiments, in terms of horizontal positions, the emitting patterns 156 are disposed under the through hole 200, and the alignment patterns 156 may be disposed under a remaining portion of the support 100.

In addition, as shown in FIG. 17, the emitting patterns 156 may be formed with an area smaller than the through hole 200. That is, the plurality of emitting patterns 156 may be formed under the through hole 200. The each emitting pattern 156 may be formed to have a width range of about 1 μm to about 200 μm. According to some embodiments, the second target layer 154 or the emitting patterns 156 may be formed of a material lighter than the first target layer 152. For example, the second target layer 154 or the emitting patterns 156 may include at least one of polymethyl methacrylate (PMMA), polydimethylsiloxane (PDMS), polyimide, photoresist, or hydrogenated amorphous silicon.

Figure 19:
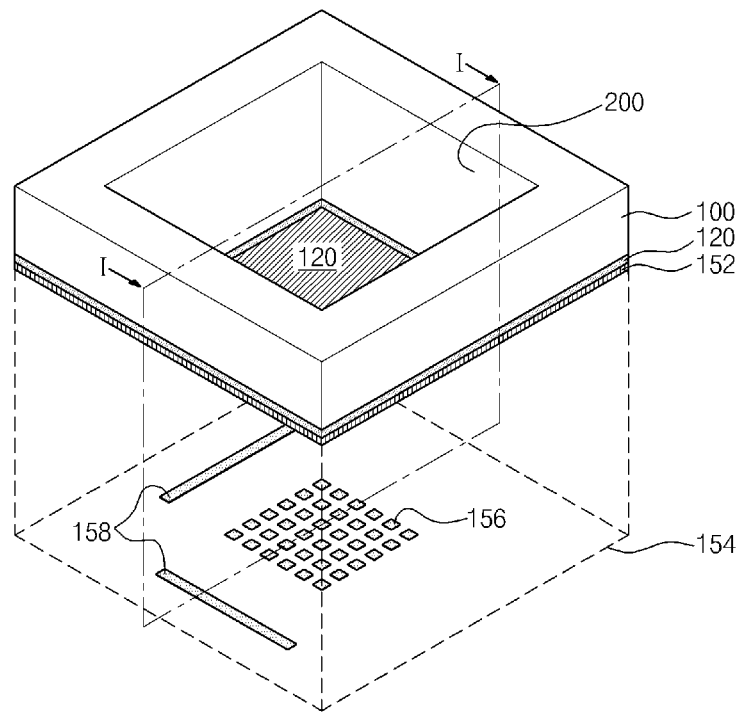
Figure 20:
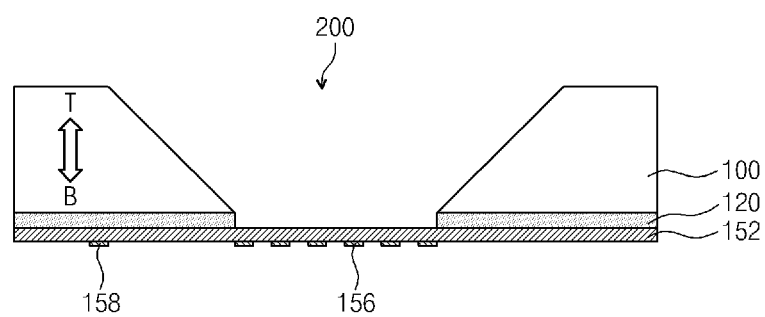

Subsequently, as shown in FIGS. 19 and 20, the first target layer 152 is exposed by etching the etch stop layer 120 exposed by the through hole 200. This operation may be performed by using the method of the foregoing embodiment described with reference to FIGS. 11 and 12.

FIGS. 21, 23, 25 and 27 are perspective views illustrating a method of manufacturing a target structure according to a fourth embodiment of the present invention, and FIGS. 22, 24, 26 and 28 are cross-sectional views illustrating the method of manufacturing a target structure according to the fourth embodiment of the present invention. In particular, FIGS. 22, 24, 26 and 28 illustrate cross-sections shown along the dotted lines 'I-I' of FIGS. 21, 23, 25 and 27, respectively. For the simplicity of the description, the description related to the technical characteristics overlapping with the foregoing first to third embodiments may not be provided.

According to the present embodiment, as described with reference to FIGS. 13 and 14, the mask pattern 110 is formed on the top surface T of the support 100, the etch stop layer 120 and the target layer is sequentially formed on the bottom surface B of the support 100, and the target layer may include a first target layer 152 and a second target layer 154 that are formed of materials different from each other.

Figure 22:
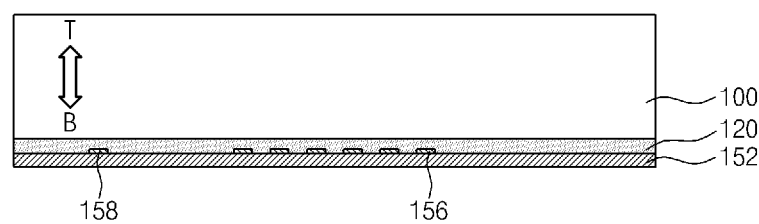
FIGS. 22, 24, 26 and 28 are cross-sectional views illustrating the method of manufacturing a target structure according to the fourth embodiment of the present invention.
Figure 23:
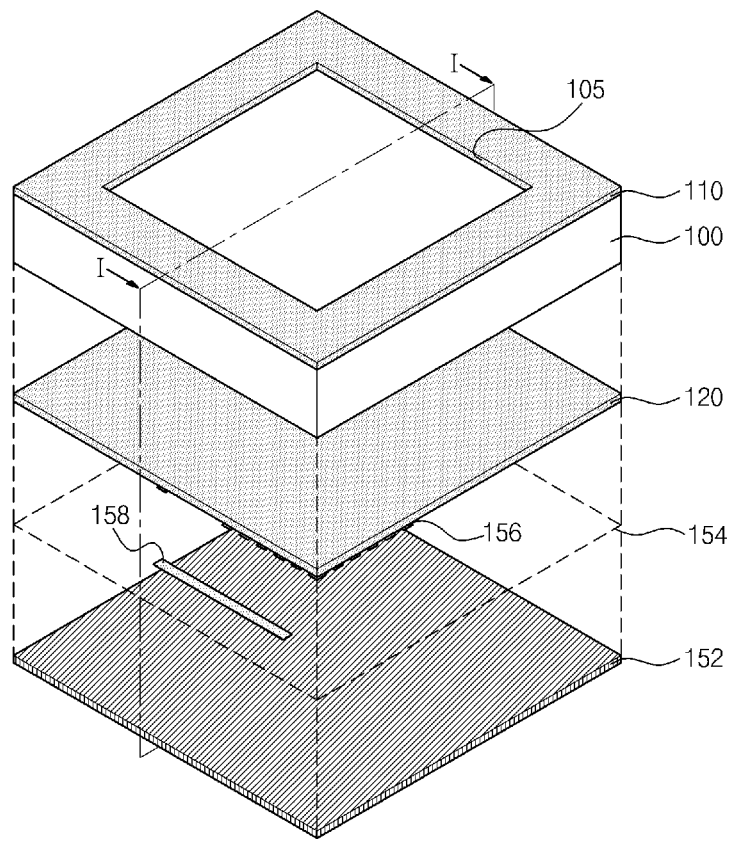
Figure 24:
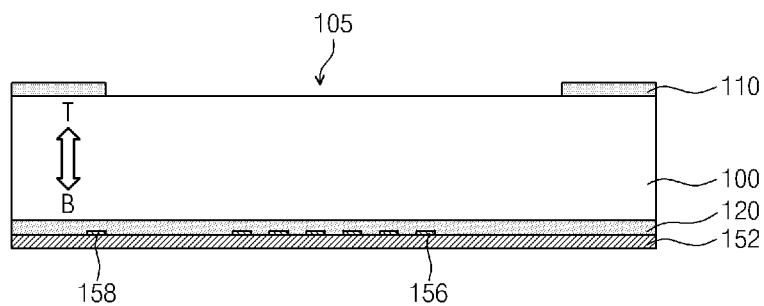

However, according to the present embodiment, the second target layer 154 may be disposed between the first target layer 152 and the etch stop layer 120 as shown in FIGS. 23 and 24. That is, the second target layer 154 may be formed before the forming of the first target layer 152. In addition, the emitting patterns 156 and the alignment patterns 158 may be formed by patterning the second target layer 154 before the forming of the first target layer 152. Technical characteristics related to materials, shape, and arrangement for the first and second target layers 152 and 154 may be the same as the foregoing embodiment described with reference to FIGS. 13, 15, 17 and 19. However, according to other embodiments, the emitting patterns 156 and the alignment patterns 158 may be formed to fill a recessed region formed on a lower surface of the etch stop layer 120 by using a damascene process as shown in FIG. 22.

Figure 21:
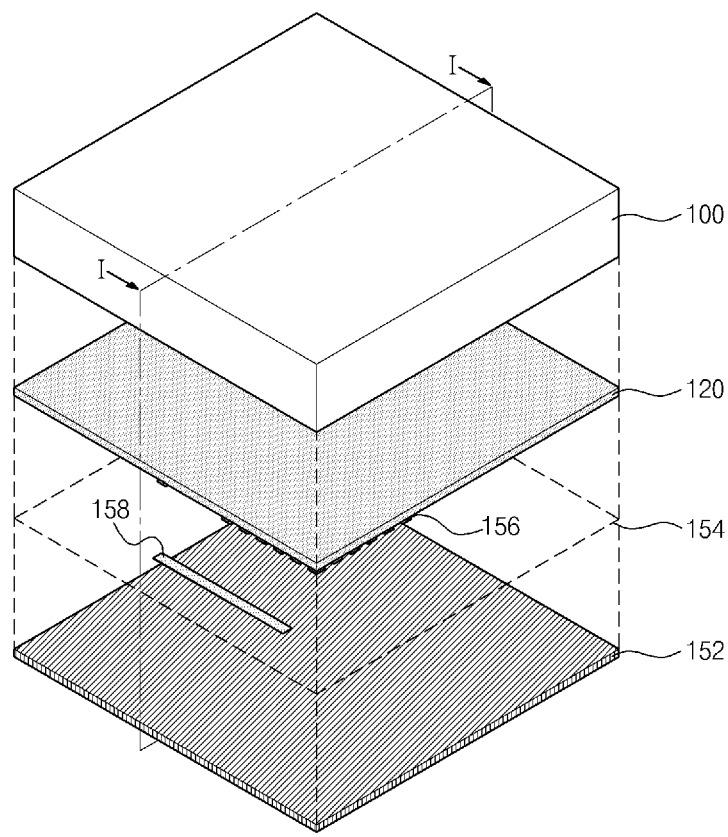
FIGS. 21, 23, 25 and 27 are perspective views illustrating a method of manufacturing a target structure according to a fourth embodiment of the present invention.

Meanwhile, according to some embodiments, the second and first target layers 154 and 152 are sequentially formed, and then the mask pattern 110 may be formed on the top surface T of the support 100 as it can be seen from the comparison between FIG. 21 and FIG. 23. However, according to other embodiments, the mask pattern 110 may be formed before the first target layer 152.

Figure 25:
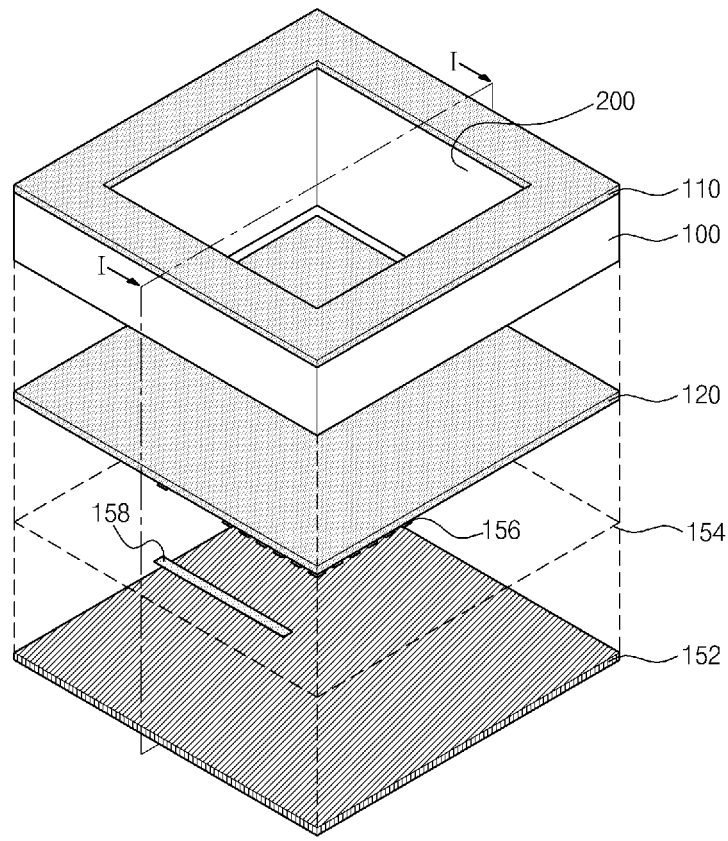
Figure 26:
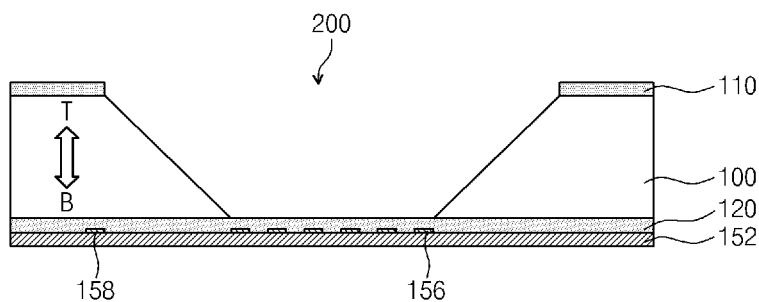

Subsequently, as shown in FIGS. 25 and 26, the through hole 200 exposing the etch stop layer 120 is formed by etching the support 100 by using the mask pattern 110 as an etch mask. Meanwhile, as described in the foregoing embodiments, since the etching damage with respect to the target layer may be prevented by the etch stop layer 120, the second target layer 154 may not have restrictions with respect to the type of a material usable. According to some embodiments, the second target layer 154 may include at least one of polymethyl methacrylate (PMMA), polydimethylsiloxane (PDMS), polyimide, photoresist, or hydrogenated amorphous silicon, and the first target layer 152 may be formed of platinum, gold, silver, aluminum, titanium, or hydrogenated amorphous silicon.

Figure 27:
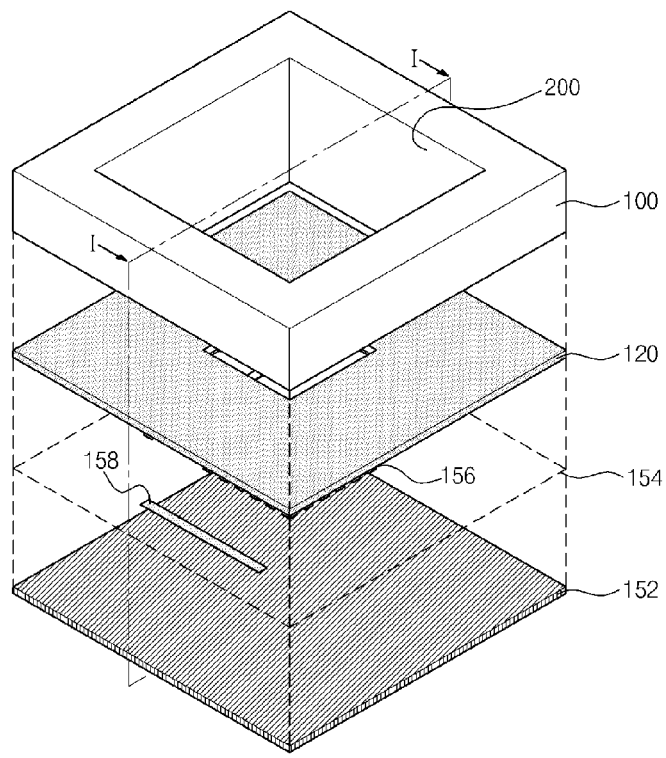
Figure 28:
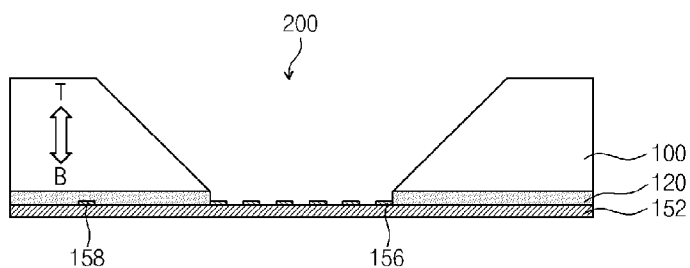

Thereafter, the target layer is exposed by selectively etching the etch stop layer 120 exposed by the through hole 200. That is, as shown in FIGS. 27 and 28, the emitting patterns 156 and the first target layer 152 positioned thereunder are exposed through the through hole 200.

FIGS. 29 through 32 are perspective views exemplarily illustrating target structures according to embodiments of the present invention. In particular, FIGS. 29 through 32 may be target structures manufactured through the manufacturing methods according to the foregoing first to fourth embodiments, respectively.

Referring to FIGS. 29 through 32, a target layer 150 is formed on one surface of a support 100. According to embodiments of the present invention, the support 100 is formed to a thickness range of about a few hundred micrometers to about a few millimeters, and the target layer 150 may be formed to a thickness range of about 0.001 μm to about 10 μm. According to some embodiments, the support 100 may be formed to a thickness of at least about 100 μm, and the target layer 150 may be formed to a thickness range of about 0.001 μm to about 1 μm. The support 100 includes a through hole 200 penetrating thereto to expose the target layer 150. According to some embodiments, the through hole 200 may be formed to have sidewalls inclined with respect to the top surface of the support 100.

According to some embodiments, the target layer 150 may be formed to directly contact the support 100 as shown in FIG.

29. In this case, the target layer 150 may be formed of at least one material having an etch selectivity with respect to the support 100. For example, the target layer 150 may be formed of platinum, gold, silver, aluminum, titanium, or hydrogenated amorphous silicon.

Figure 30:
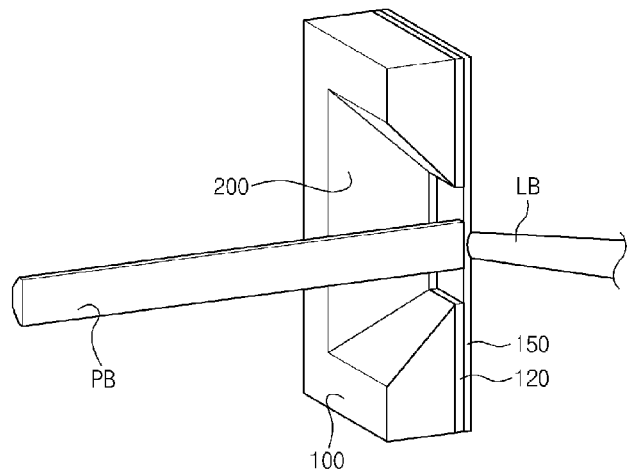
Figure 31:
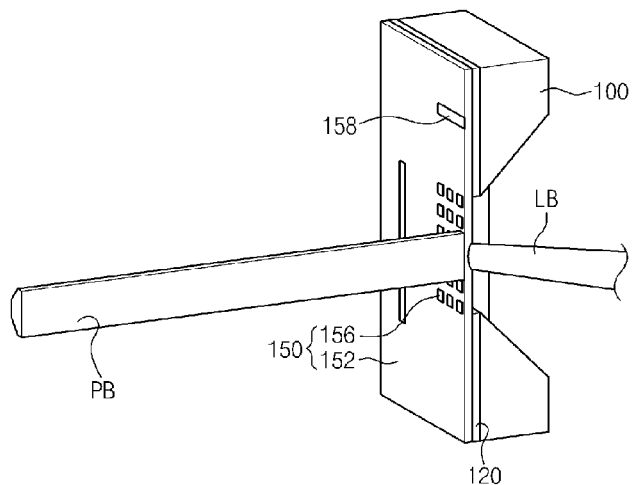
Figure 32:
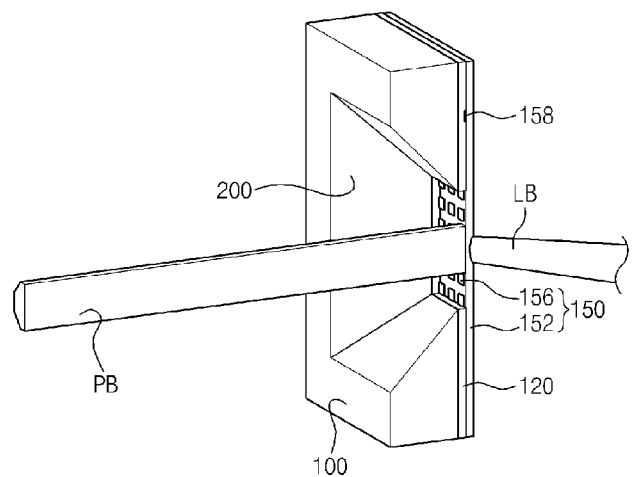

Meanwhile, according to other embodiments, an etch stop layer 120 may be further disposed between the support 100 and the target layer 150 as shown in FIGS. 30 through 32. When the etch stop layer 120 is formed, technical limitations in that the target layer 150 has etching damages during the forming of the through hole 200 may be prevented. Therefore, a material for the target layer 150 may be freely selected without substantial restrictions. For example, according to the foregoing embodiments, the target layer 150 may be at least one of inert metals, aluminum, titanium, polymethyl methacrylate (PMMA), polydimethylsiloxane (PDMS), polyimide, photoresist, or hydrogenated amorphous silicon.

Figure 29:
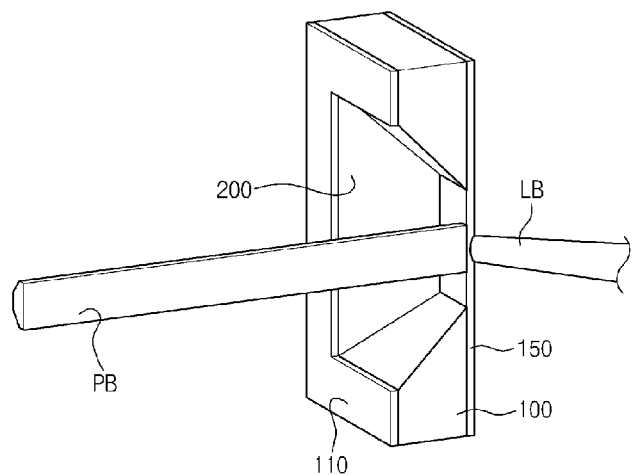
FIGS. 29 through 32 are perspective views exemplarily illustrating target structures according to embodiments of the present invention.

The target layer 150 may have a single-layer structure as shown in FIGS. 29 and 30 or a multilayer structure including emitting patterns 156 and alignment patterns 158 formed on one surface of the first target layer 152 as shown in FIGS. 31 and 32. When the target layer 150 has a multilayer structure, the first target layer 152 is formed of one inert metal, the emitting patterns 156 may be formed of at least one material lighter than the first target layer 152 (e.g., aluminum, titanium, PMMA, PDMS, polyimide, photoresist, or hydrogenated amorphous silicon).

In addition, when the target layer 150 has a multilayer structure, a laser beam LB is radiated to the first target layer 152 and a charged particle beam PB may be emitted from the emitting patterns 156. That is, as shown in FIG. 31, the laser beam LB may be incident on the first target layer 152 through the through hole 200 when the first target layer 152 is disposed between the emitting patterns 156 and the support 100. Also, as shown in FIG. 32, the charged particle beam PB may be emitted through the through hole 200 when the emitting patterns 156 are disposed between the first target layer 152 and the support 100. The alignment patterns 158 may be used to adjust a relative position between the laser beam LB and the support 100.

Figure 33:
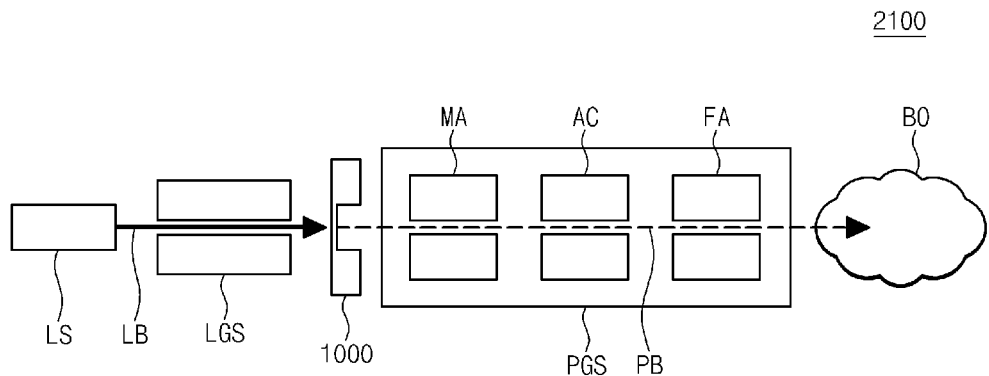
FIGS. 33 and 34 exemplarily illustrate an apparatus for generating a charged particle beam from the target structure of the present invention.
Figure 34:
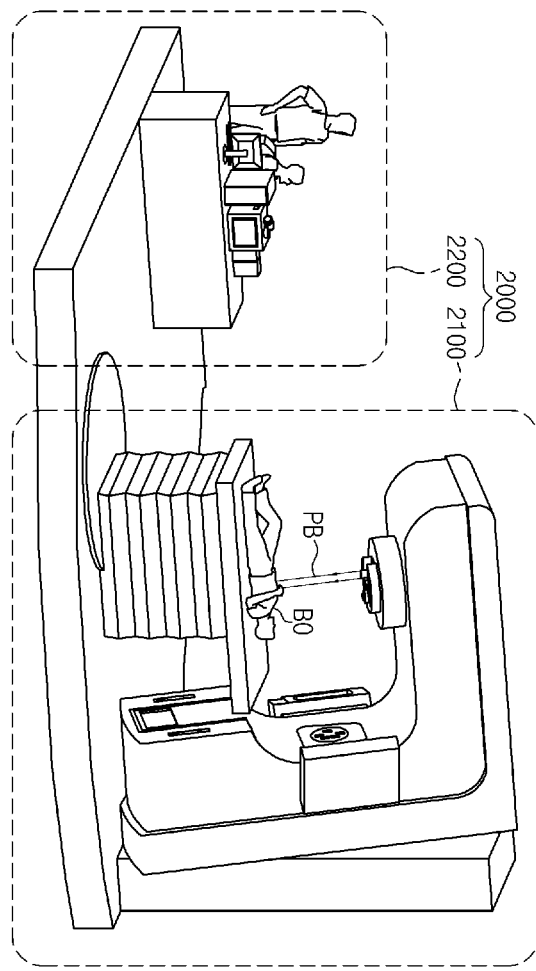

FIGS. 33 and 34 exemplarily illustrate an apparatus for generating a charged particle beam from the target structure of the present invention.

Referring to FIG. 33, an apparatus 2100 may include a light source LS generating a laser beam LB and a target structure 1000 irradiated by the laser beam LB. The target structure 1000 may be one manufactured through the embodiments described with reference to FIGS. 1 through 28 or one described with reference to FIGS. 29 through 32.

In addition, the apparatus 2100 may include a light guide structure LGS guiding the laser beam LB to the target structure 1000 and a charged particle beam guide structure PGS guiding the charged particle beam PB emitted from the target structure 1000 to a biological object BO. The light guide structure LGS is disposed between the light source LS and the target structure 1000 and may include a lens and/or a reflector. The charged particle beam guide structure PGS is disposed between the target structure 1000 and the biological object BO and may include at least one of a mass analyzer MA, an accelerator AC, or a focusing apparatus FA.

Meanwhile, the light source LS generates a high-power pulsed laser of at least about $10^{13}$ watt and the light guide structure LGS may be configured for the laser beam LB to have an intensity of about $10^{18}$ W/cm$^2$ and incident on the target structure 1000. In this case, the charged particle beam PB may be generated through one of a target normal sheath acceleration (TNSA) mechanism or a radiation pressure acceleration (RPA) mechanism. More particularly, when the intensity of the laser beam LB incident on the target structure 1000 is in a range of about $10^{18}$ W/cm$^2$ to about $10^{19}$ W/cm$^2$, the charged particle beam PB is generated thorough the TNSA mechanism and is emitted along a direction perpendicular to a surface of the target layer 150 as shown in FIGS. 29 and 32. However, when the intensity of the laser beam LB is about $10^{20}$ W/cm$^2$ or more, the charged particle beam PB is generated thorough the RPA mechanism and is emitted along a direction parallel to an incident direction of the laser beam LB.

In addition, when the target layer is formed to a thickness smaller than about 1 μm, the light source LS may generate a laser having a high contrast ratio of at least about $10^{10}$. When a laser having such a high contrast ratio is used, a shock wave due to the amplified spontaneous emission (ASE) of a laser may be reduced. The reduction of the shock wave enables to decrease the thickness of the target layer to about 1 μm or less.

The apparatus 2100 generating a charged particle beam described with reference to FIG. 33 may constitute a medical appliance 2000 for curing malignant tumors in a biological object BO as shown in FIG. 34. The medical appliance 2000 may further include a controller 2200 configured to control the charged particle beam generating apparatus 2100 as well as providing a user interface.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

The invention claimed is:

1. A target structure comprising:
    a target layer having a first surface irradiated by a laser beam and a second surface emitting a charged particle beam;
    a support having a through hole used as a progressing path of the laser beam or the charged particle beam; and
    an intermediate layer disposed between the target layer and the support,
    wherein the intermediate layer has an intermediate through hole exposing the target layer and the intermediate through hole is aligned to the through hole of the support.

2. The target structure of claim 1, wherein the through hole is used as the progressing path of the laser beam.

3. The target structure of claim 1, wherein the through hole is used as the progressing path of the charged particle beam.

4. The target structure of claim 1, wherein the target layer is formed to a thickness range of about 0.001 μm to about 10 μm, and the support comprises at least one of silicon, sapphire, diamond, quartz, glass, ceramic materials, or metallic materials and is formed to a thickness of at least about 100 μm.

5. The target structure of claim 1, wherein the support comprises a material having a single crystal structure, and a surface of the support is a (100) plane.

6. The target structure of claim 5, wherein the through hole comprises a region having a width that gradually increases away from the target layer.

7. The target structure of claim 1, wherein the target layer comprises at least one inert metal.

8. The target structure of claim 1, wherein the target layer comprises at least one of inert metals, aluminum, titanium, polymethyl methacrylate (PMMA), polydimethylsiloxane (PDMS), polyimide, photoresist, or hydrogenated amorphous silicon.

9. The target structure of claim 1, wherein the target layer comprises a first target layer and a second target layer formed of materials different from each other,
   wherein the first target layer constitutes the first surface irradiated by the laser beam and the second target layer constitutes the second surface emitting the charged particle beam.

10. The target structure of claim 9, wherein the first target layer is formed of at least one metallic material and the second target layer is formed of at least one of polymethyl methacrylate (PMMA), polydimethylsiloxane (PDMS), polyimide, photoresist, or hydrogenated amorphous silicon.

11. The target structure of claim 1, wherein the second surface comprises a plurality of emitting patterns.

* * * * *